United States Patent
Hengstermann et al.

(10) Patent No.: US 7,807,826 B2
(45) Date of Patent: Oct. 5, 2010

(54) PURIFICATION OF A CRUDE LACTAM MIXTURE BY MEANS OF MELT CRYSTALLIZATION

(75) Inventors: Axel Hengstermann, Senden (DE); Ralf Meier, Dortmund (DE); Bernd Günzel, Haltern am See (DE); Martin Roos, Haltern am See (DE); Stephan Schäflein, Haltern am See (DE); Bernd-Holger Modrow, Herne (DE)

(73) Assignee: Evonik Degussa GmbH, Essen (DE)

( * ) Notice: Subject to any disclaimer, the term of this patent is extended or adjusted under 35 U.S.C. 154(b) by 0 days.

(21) Appl. No.: 12/244,452

(22) Filed: Oct. 2, 2008

(65) Prior Publication Data

US 2009/0088567 A1    Apr. 2, 2009

(30) Foreign Application Priority Data

Oct. 2, 2007    (DE) .................. 10 2007 047 322

(51) Int. Cl.
*C07D 225/00* (2006.01)
(52) U.S. Cl. .................................... 540/451
(58) Field of Classification Search ................. 540/451
See application file for complete search history.

(56) References Cited

U.S. PATENT DOCUMENTS

| | | | | | |
|---|---|---|---|---|---|
| 3,839,324 | A | * | 10/1974 | Schultze et al. | 540/540 |
| 4,248,781 | A | * | 2/1981 | Horn et al. | 540/540 |
| 6,596,862 | B2 | * | 7/2003 | Bottcher et al. | 540/540 |

\* cited by examiner

*Primary Examiner*—Bruck Kifle
(74) *Attorney, Agent, or Firm*—Oblon, Spivak, McClelland, Maier & Neustadt, L.L.P.

(57) ABSTRACT

The present invention provides a method for purifying laurolactam from a crude lactam mixture. In the method of the present invention, laurolactam is selectively crystallized by melt crystallization with controlled cooling of the crude lactam mixture.

18 Claims, No Drawings

PURIFICATION OF A CRUDE LACTAM MIXTURE BY MEANS OF MELT CRYSTALLIZATION

CROSS-REFERENCE TO RELATED APPLICATIONS

The present application claims priority to German Application No. DE 102007047322.4, filed on Oct. 2, 2007, which is hereby incorporated by reference in its entirety.

BACKGROUND OF THE INVENTION

1. Field of the Invention

The present invention provides a method for the purification of a crude lactam mixture by means of melt crystallization. In the present invention, the crude lactam mixture contains laurolactam as the target component and secondary components. As the mixture is cooled, the laurolactam selectively crystallizes and can be removed from the mixture.

2. Discussion of the Background

Laurolactam is typically removed from the secondary components in a crude lactam mixture by means of a multistage distillation. Due to the high boiling point of laurolactam, during distillation a high vacuum has to be applied. However, the thermal stress on the mixture in every evaporation step leads to the decomposition of the material of value. Thus, the method heretofore employed in the art described above, leads to a reduction in the overall yield of laurolactam.

SUMMARY OF THE INVENTION

It is an object of the present invention to provide

[1] A process for purifying a crude lactam mixture, comprising selectively crystallizing laurolactam present in said crude lactam mixture by melt crystallization through controlled cooling of said crude lactam mixture.

[2] The process according to [1], wherein said melt crystallization is layer crystallization.

[3] The process according to [2], wherein the melt crystallization is conducted with a moving melt at the inner walls of a cooled tube.

[4] The process according to [3], wherein the movement of the melt is generated on the inside of a cooled tube by means of a trickle film.

[5] The process according to [3], wherein the movement of the melt is generated on the inside of a cooled tube by means of full flow through the tube.

[6] The process according to [2], wherein the melt crystallization is conducted with a moving melt at the outer walls of a cooled tube.

[7] The process according to [6], wherein the movement of the melt is generated on the outside of a cooled tube by means of a trickle film.

[8] The process according to [2], wherein the layer crystallization further comprises a mobile or immobile melt on the outsides of cooled heat exchanger plates.

[9] The process according to [2], wherein said layer crystallization comprises controlled increase in the wall temperature to partially melt a crystal layer which contains the laurolactam and intercalated secondary components to sweat adhering secondary components out of the crystal layer.

[10] The process according to [1], wherein said melt crystallization is suspension crystallization.

[11] The process according to [8], wherein a suspension is generated by heat exchangers with a scraped heat exchanger surface.

[12] The process according to [8], wherein particles generated during said suspension crystallization are removed from the mother liquor by a solid/liquid separation and are washed with a molten product.

[13] The process according to [12], wherein said solid/liquid separation is performed with a centrifuge.

[14] The process according to [8], wherein a suspension is introduced into a hydraulic, mechanical or gravimetric wash column in which the particles are separated from the mother liquor and washed in countercurrent with a molten product.

[15] The process according to [1], wherein the purity is increased by crystallizing the resulting crystal fraction at least once.

[16] The process according to [1], wherein the yield is enhanced by crystallizing the mother liquor removed at least once.

[17] The process according to [1], wherein simultaneously the purity is increased and the yield is enhanced, wherein the purity is increased by crystallizing the resulting crystal fraction at least once and wherein the yield is enhanced by crystallizing the mother liquor removed at least once.

The above objects highlight certain aspects of the invention. Additional objects, aspects and embodiments of the invention are found in the following detailed description of the invention.

DETAILED DESCRIPTION OF THE INVENTION

Unless specifically defined, all technical and scientific terms used herein have the same meaning as commonly understood by a skilled artisan in organic chemistry.

All methods and materials similar or equivalent to those described herein can be used in the practice or testing of the present invention, with suitable methods and materials being described herein. All publications, patent applications, patents, and other references mentioned herein are incorporated by reference in their entirety. In case of conflict, the present specification, including definitions, will control. Further, the materials, methods, and examples are illustrative only and are not intended to be limiting, unless otherwise specified.

The present invention provides a thermal separating process, particularly for laurolactam from a crude lactam mixture, which satisfies the following boundary conditions:
  reduction of the thermal stress on the product by reducing the number of thermal separating steps needed, and
  reduction of the thermal stress by lowering the process temperature needed.

The present inventors have discovered that laurolactam can be selectively crystallized by controlled cooling of the crude lactam mixture. Crystal formation of a crude lactam mixture is observed at a temperature of 141.5° C. After removal of the mother liquor and purification of the crystals by partial melting, a colorless crystal fraction is obtained. The melting point of the crystal fraction is at a temperature of 151.7° C., which corresponds to the melting point of pure laurolactam.

Within the scope of the present invention, laurolactam may be produced as described in, for example, the Römpp online encyclopedia and the references cited therein including Weissermel-Arpe (5.), S. 288ff; Beilstein EV 21/6, 566; Lepifre et al, Tetrahedron (2001) 57, 6969-6975; and Ullmann (6.) [CD-ROM, 1998].

Thus, the crystallization of laurolactam from the crude lactam mixture can be conducted industrially by means of layer or suspension crystallization.

In layer crystallization, the wall temperature is lowered in a controlled manner to induce crust formation. The crust formation on the surface establishes the necessary heat transfer. The solid deposited contains the desired target product and intercalated secondary components. The uncrystallized residual melt is then discharged providing a remaining crystal layer. The controlled wall temperature increase partially melts the crystal layer, which "sweats" adhering secondary components out of the crystal layer. As soon as the wall temperature is raised to a point above the melting point of the target product, the target lo product can be removed from the system in the liquid state.

In the present invention, layer crystallization is conducted batchwise and can be carried out with a mobile (dynamic) or immobile (static) melt. Dynamic layer crystallizations may, as desired, be a moving melt conducted on the inside or outside of cooled tubes. At the same time, turbulent motion of the melt can be accomplished in the form of a trickle film on the inside or outside of the tube or by means of full flow on the inside of the tube. Static layer crystallization is generally implemented on the outside of heat exchanger plates immersed into vessels. According to the apparatus manufacturer, the initially charged melt is stirred in static mode or stored at rest in the crystalizer.

In suspension crystallization, the solid phase, predominantly comprising the target product, is generated as dispersed particles in the melt. The heat is removed via cooled heat-exchange surfaces. In this case, however, crust formation on the surface is prevented by the use of so-called scraped coolers. As a result of the large specific particle surface area, the crystals in the suspension grow significantly more slowly than in the melt crystallization and, therefore, have only a very low secondary component concentration. A downstream solid/liquid separation is implemented to remove the particles from the liquid phase. In order to remove the adhering mother liquor from the crystal surface, a crystal wash with an already molten product is conducted. To this end, it is possible to use conventional solid/liquid separating devices or wash columns developed especially for melt crystallization. The product purities in the suspension crystallization are based on low growth rates depending predominantly on the downstream wash process.

In the present invention, the laurolactam purity may be increased by crystallizing the resulting crystal fraction at least once. Further, in the present invention, the yield may be enhanced by crystallizing the mother liquor removed at least once. Within the present invention, the purity and yield may be independently increased, increased in series, or simultaneously increased. It would be appreciated by the skilled artisan that "at least once" means 1 or more times. With respect to "more times", the present invention contemplates, for example 2 to 10 times and 2 to five times.

The above written description of the invention provides a manner and process of making and using it such that any person skilled in this art is enabled to make and use the same, this enablement being provided in particular for the subject matter of the appended claims, which make up a part of the original description.

As used above, the phrases "selected from the group consisting of," "chosen from," and the like include mixtures of the specified materials.

Where a numerical limit or range is stated herein, the endpoints are included. Also, all values and subranges within a numerical limit or range are specifically included as if explicitly written out.

The above description is presented to enable a person skilled in the art to make and use the invention, and is provided in the context of a particular application and its requirements. Various modifications to the preferred embodiments will be readily apparent to those skilled in the art, and the generic principles defined herein may be applied to other embodiments and applications without departing from the spirit and scope of the invention. Thus, this invention is not intended to be limited to the embodiments shown, but is to be accorded the widest scope consistent with the principles and features disclosed herein.

Having generally described this invention, a further understanding can be obtained by reference to certain specific examples, which are provided herein for purposes of illustration only, and are not intended to be limiting unless otherwise specified.

EXAMPLES

Example 1

The test apparatus consisted of an inertizable jacketed vessel with a volume of 750 ml. The jacketed vessel was equipped with a temperature-controllable metal cooling finger. The jacketed vessel was heated by means of a liquid heat carrier oil at a temperature of 160° C. The temperature of the jacketed vessel was controlled by means of a regulatable heat carrier circuit. The metal cooling finger extended to an extent of approx. 75% into the liquid crude lactam mixture. The surface temperature of the metal cooling finger was determined with a Pt 100 temperature sensor.

The jacketed vessel was charged with 650 g of the crude lactam mixture and inertized with nitrogen. The flow temperature of the heat carrier oil to heat the jacketed vessel was set to 160° C. The flow temperature to control the temperature of the metal cooling finger was set to 155° C. Subsequently, the flow temperature of the metal cooling finger was reduced stepwise with a temperature gradient of 0.2 K/min. At a surface temperature of 141.5° C., the first crystals were deposited on the surface of the metal cooling finger. Once a crystal layer of 0.5-0.7 cm had been achieved, the temperature gradient was stopped. Subsequently, the liquid mother liquor was discharged form the vessel and its mass was determined.

To purify the crystal layer, the flow temperature of the metal cooling finger was raised stepwise with a temperature gradient of 0.2 K/min. Just before the melting point of pure laurolactam was attained, the sweating fraction obtained was discharged from the jacketed vessel and likewise weighed. The crystal layer which remained on the metal cooling finger was melted completely by raising the flow temperature, discharged and weighed. The experimental results are reported below.

| Designation | Mass | Laurolactam | CDON | Residue |
| --- | --- | --- | --- | --- |
| Feed | 649.7 g | 89.0% | 7.6% | 3.4% |
| Mother liquor | 383.8 g | 88.0% | 8.4% | 3.6% |
| Sweating fraction | 208.9 g | 91.0% | 6.3% | 2.9% |
| Crystal fraction | 38.8 g | 98.3% | 1.1% | 0.6% |

The advantages of purifying laurolactam from a crude lactam mixture via melt crystallization include:

The thermal stress on the product based on the lower temperature level of the melt crystallization is lower than in the distillative separation and the thermal decomposition is thus reduced.

No high vacuum has to be applied as in the case of distillative separation steps, which achieves an additional reduction in the energy costs.

The number of thermal separating steps to achieve the target quality is lower as a result of the high selectivity of crystallization.

The reduction in the thermal separating steps reduces the complexity of the workup sequence and thus eases usability.

The energy use needed is reduced, since the melting enthalpy is lower than the evaporation enthalpy.

The high selectivity of the crystallization with few separation steps allows the necessary colour number to be attained.

The sublimation tendency of the pure material during the crystallization operation can be reduced and additionally does not impair the process, as occurs in gas-conducting components in distillation columns.

Numerous modifications and variations on the present invention are possible in light of the above teachings. It is, therefore, to be understood that within the scope of the accompanying claims, the invention may be practiced otherwise than as specifically described herein.

The invention claimed is:

1. A process for purifying a crude lactam mixture, comprising
selectively crystallizing laurolactam present in said crude lactam mixture by melt crystallization through controlled cooling of said crude lactam mixture.

2. The process according to claim 1, wherein said melt crystallization is layer crystallization.

3. The process according to claims 2, wherein the melt crystallization is conducted with a moving melt at the inner walls of a cooled tube.

4. The process according to claim 3, wherein the movement of the melt is generated on the inside of a cooled tube by means of a trickle film.

5. The process according to claim 3, wherein the movement of the melt is generated on the inside of a cooled tube by means of full flow through the tube.

6. The process according to claim 2, wherein the melt crystallization is conducted with a moving melt at the outer walls of a cooled tube.

7. The process according to claim 6, wherein the movement of the melt is generated on the outside of a cooled tube by means of a trickle film.

8. The process according to claim 2, wherein the layer crystallization further comprises a mobile or immobile melt on the outsides of cooled heat exchanger plates.

9. The process according to claim 2, wherein said layer crystallization comprises controlled increase in the wall temperature to partially melt a crystal layer which contains the laurolactam and intercalated secondary components to sweat adhering secondary components out of the crystal layer.

10. The process according to claim 1, wherein said melt crystallization is suspension crystallization.

11. The process according to claim 8, wherein a suspension is generated by heat exchangers with a scraped heat exchanger surface.

12. The process according to claim 8, wherein particles generated during said suspension crystallization are removed from the mother liquor by a solid/liquid separation and are washed with a molten product.

13. The process according to claim 12, wherein said solid/liquid separation is performed with a centrifuge.

14. The process according to claim 8, wherein a suspension is introduced into a hydraulic, mechanical or gravimetric wash column in which the particles are separated from the mother liquor and washed in countercurrent with a molten product.

15. The process according to claim 1, wherein the purity is increased by crystallizing the resulting crystal fraction at least once.

16. The process according to claim 1, wherein the yield is enhanced by crystallizing the mother liquor removed at least once.

17. The process according to claim 1, wherein simultaneously the purity is increased and the yield is enhanced, wherein the purity is increased by crystallizing the resulting crystal fraction at least once and wherein the yield is enhanced by crystallizing the mother liquor removed at least once.

18. The process according to claim 3, wherein the cooled tube comprises a metal cooling finger and wherein said process further comprises:
forming first crystals of laurolactam on the surface of the metal cooling finger when a surface temperature of the metal cooling finger is reduced from a first temperature to 141.5° C. at a rate of 0.2 K/min,
discharging a liquid mother liquor from the cooled tube upon formation of the crystals in a layer having a thickness of from 0.5 cm to 0.7 cm,
increasing the temperature of the metal cooling finger at a rate of 0.2 K/min up to a second temperature just below the melting point of pure laurolactam, thereby forming a sweat fraction comprising secondary components other than laurolactam,
discharging the sweat fraction from the cooled tube,
increasing the temperature of the metal cooling finger until the layer of crystals formed on the metal cooling finger is melted, and
discharging and recovering the melted crystals of pure laurolactam.

* * * * *